(12) United States Patent
Jeon et al.

(10) Patent No.: US 10,766,019 B2
(45) Date of Patent: Sep. 8, 2020

(54) OLEFIN METATHESIS REACTION CATALYST AND PREPARATION METHOD THEREFOR

(71) Applicant: KOREA RESEARCH INSTITUTE OF CHEMICAL TECHNOLOGY, Daejeon (KR)

(72) Inventors: Jong Yeol Jeon, Daejeon (KR); Man Jae Gil, Daejeon (KR); Dong Won Hwang, Daejeon (KR); Young Kyu Hwang, Daejeon (KR); Yoo Han Han, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 16/329,469

(22) PCT Filed: Nov. 9, 2017

(86) PCT No.: PCT/KR2017/012660
§ 371 (c)(1),
(2) Date: Feb. 28, 2019

(87) PCT Pub. No.: WO2018/088815
PCT Pub. Date: May 17, 2018

(65) Prior Publication Data
US 2019/0217277 A1  Jul. 18, 2019

(30) Foreign Application Priority Data
Nov. 9, 2016  (KR) ........................ 10-2016-0148736

(51) Int. Cl.
| | |
|---|---|
| *C07C 6/04* | (2006.01) |
| *B01J 23/36* | (2006.01) |
| *B01J 37/02* | (2006.01) |
| *B01J 23/28* | (2006.01) |
| *B01J 37/08* | (2006.01) |
| *B01J 31/12* | (2006.01) |
| *B01J 21/08* | (2006.01) |
| *B01J 21/04* | (2006.01) |
| *B01J 23/40* | (2006.01) |
| *B01J 23/745* | (2006.01) |
| *B01J 23/75* | (2006.01) |
| *B01J 23/06* | (2006.01) |
| *B01J 23/656* | (2006.01) |
| *B01J 23/20* | (2006.01) |
| *B01J 29/03* | (2006.01) |

(Continued)

(52) U.S. Cl.
CPC ............... *B01J 23/36* (2013.01); *B01J 21/04* (2013.01); *B01J 21/08* (2013.01); *B01J 23/06* (2013.01); *B01J 23/08* (2013.01); *B01J 23/20* (2013.01); *B01J 23/28* (2013.01); *B01J 23/40* (2013.01); *B01J 23/6567* (2013.01); *B01J 23/745* (2013.01); *B01J 23/75* (2013.01); *B01J 29/0333* (2013.01); *B01J 29/0341* (2013.01); *B01J 31/12* (2013.01); *B01J 37/0207* (2013.01); *B01J 37/0209* (2013.01); *B01J 37/08* (2013.01); *C07C 6/04* (2013.01); *B01J 21/12* (2013.01); *B01J 2231/543* (2013.01); *C07C 2523/08* (2013.01); *C07C 2523/14* (2013.01); *C07C 2523/20* (2013.01); *C07C 2523/28* (2013.01); *C07C 2523/36* (2013.01); *C07C 2523/46* (2013.01); *C07C 2523/745* (2013.01); *C07C 2523/75* (2013.01)

(58) Field of Classification Search
CPC .................................... C07C 6/04; B01J 23/36
See application file for complete search history.

(56) References Cited

U.S. PATENT DOCUMENTS

| | | | |
|---|---|---|---|
| 4,275,052 A | * | 6/1981 | Ryu ........................ B01J 21/04 423/628 |
| 4,748,145 A | | 5/1988 | Wood et al. |

(Continued)

FOREIGN PATENT DOCUMENTS

| | | |
|---|---|---|
| KR | 10-0589500 B1 | 6/2006 |
| KR | 10-2011-0123051 A | 11/2011 |

(Continued)

OTHER PUBLICATIONS

Oikawa, Takashi, et al., "A new heterogeneous olefin metathesis catalyst composed of rhenium oxide and mesoporous alumina", Microporous and Mesoporous Materials, Aug. 7, 2004, vol. 74, pp. 93-103.

(Continued)

*Primary Examiner* — Stuart L Hendrickson
(74) *Attorney, Agent, or Firm* — Workman Nydegger (57) ABSTRACT

The present invention relates to an olefin metathesis reaction catalyst where rhenium (Re) oxide or molybdenum (Mo) oxide is supported, as a catalyst main component, on a surface-modified mesoporous silica or mesoporous alumina support, and a preparation method therefor. The olefin metathesis reaction catalyst of the present invention allows highly efficient metathesis of long-chain unsaturated hydrocarbons having at least eight carbons at a low temperature of 150° C. or lower. The catalyst can be separated readily from reaction solution, regenerated at a low temperature of 400° C. or lower by removing toxins accumulated on it during the metathesis reaction, and used repeatedly in metathesis reaction many times, thereby being made good use in commercial olefin metathesis processes.

10 Claims, 1 Drawing Sheet

(51) Int. Cl.
  *B01J 23/08*  (2006.01)
  *B01J 21/12*  (2006.01)

(56) References Cited

U.S. PATENT DOCUMENTS

| | | | | |
|---|---|---|---|---|
| 5,905,055 | A * | 5/1999 | Verdonck | B01J 23/20 |
| | | | | 502/152 |
| 8,993,823 | B2 * | 3/2015 | Taoufik | C07C 6/04 |
| | | | | 502/152 |
| 9,365,765 | B2 * | 6/2016 | LeViness | C09K 8/68 |
| 9,656,247 | B2 * | 5/2017 | Daly | B01J 37/18 |

FOREIGN PATENT DOCUMENTS

| | | |
|---|---|---|
| KR | 10-1272392 B1 | 6/2013 |
| KR | 10-2014-0033383 A | 3/2014 |

OTHER PUBLICATIONS

Z Vit. and L. Nondek, "Determination of the Surface Hydroxy Groups on Alumina and Silica-Alumina Catalysts by Dimethylzinc" Institute of Chemical Process Fundamentals, Czechoslovak Academy of Sciences, 165 02 Prague 6, Czechoslovakia. React Kinet. Catal. Lett., vol. 24, 1-2, pp. 137-139 (1984).

* cited by examiner

OLEFIN METATHESIS REACTION CATALYST AND PREPARATION METHOD THEREFOR

CROSS-REFERENCE TO RELATED APPLICATIONS

This application claims priority to PCT Application No. PCT/KR2017/012660 filed Nov. 9, 2017, entitled "Olefin Metathesis Reaction Catalyst and Preparation Method Therefor," which claims the benefit of and priority to Korean Patent Application No. 10-2016-0148736, filed on Nov. 9, 2016. All the aforementioned applications are incorporated by reference herein in their entirety.

BACKGROUND OF THE INVENTION

1. Field of the Invention

The present invention relates to an olefin metathesis catalyst and a preparation method therefor

2. Description of the Related Art

Olefin metathesis reaction is mainly classified into cross metathesis, ring-opening metathesis, ring-closing metathesis, intramolecular metathesis, diene metathesis polymerization and ring-opening metathesis polymerization. Among them, olefin cross metathesis is a reaction that two olefins convert into new olefins by exchanging alkyl groups linked by double bonds as shown in formula 1.

$A=B+C=D \rightarrow A=C+B+D$, or $A=D+B=C$ (Formula 1)

Of such cross metathesis, a reaction between two identical olefin molecules is particularly referred to as self-metathesis.

Catalysts used in olefin metathesis reaction are exemplified by metal carbene-based liquid catalysts developed by Nobel laureates in chemistry and metal oxide-based solid catalysts which have been conventionally used in commercial processes.

The metal carbene-based catalyst which is in the liquid state during the reaction has an excellent catalytic activity but a problem of being weak in the presence of functional groups such as acid, ester and alcohol groups and by moisture and heat. So, under such a condition, the catalytic activity degrades gradually so that the catalyst cannot be used for a long time and the separation and recovery of the used catalyst is also difficult. To overcome the problems above, heterogeneous catalysts have been developed in which metal carbene components are attached on the surface of silica, alumina, or porous polymer. However, a catalyst that can be repeatedly used 30 times or more has not been developed yet because the metal carbene component has low chemical stability.

In the meantime, metal oxide-based solid catalysts prepared by supporting metal oxides (Re, Mo, W, etc.) on supports such as silica and alumina have high thermal and chemical stability but still have a disadvantage of low activity and high metathesis reaction temperature of 200-500° C. In relation to the metal silica or alumina catalyst, a catalyst for Fischer-Tropsch process was developed by using a mesoporous silica structure on which active metals such as cobalt, iron and nickel were supported (patent reference 1). However, a catalyst that is economical and efficient for olefin metathesis reaction has not been developed yet.

Therefore, it is requested to develop a metal oxide-based solid catalyst which has a strong catalytic activity enough to utilize in commercial process of olefin metathesis, can be used for a long time due to excellent thermal and chemical stability and can be easily separated and recovered.

The present inventors have studied on a catalyst for olefin metathesis reaction. In the course of our study, the present inventors confirmed that an olefin metathesis catalyst prepared by supporting rhenium oxide or molybdenum oxide as a catalyst main component on a mesoporous support surface-modified by a metal alkoxy compound was able to be used for metathesis of long-chain unsaturated hydrocarbons, having at least eight carbons, at a low temperature of 150° C. or lower. The catalyst was also confirmed capable of being readily separated/recovered from reaction solution, regenerated by removing toxins deteriorating its activity with oxidation at a low temperature of 400V or lower, and thereby used repeatedly for a long time, leading to the completion of the present invention.

PRIOR ART REFERENCE

Patent Reference (Patent Reference 1) Korean Patent Publication No. 10-2011-0123051

SUMMARY OF THE INVENTION

It is an object of the present invention to provide an olefin metathesis catalyst.

It is another object of the present invention to provide a preparation method of the olefin metathesis catalyst above.

To achieve the above objects, the present invention provides an olefin metathesis catalyst, in which rhenium (Re) oxide or molybdenum (Mo) oxide is supported on a mesoporous silica surface-modified by a compound in which one or more $C_1$-$C_5$ alkoxy groups are linked to one or more metals selected from the group consisting of Al, Nb, Fe, Co, Zn, Ga and Sn.

The present invention also provides an olefin metathesis catalyst, in which rhenium (Re) oxide or molybdenum (Mo) oxide is supported on a mesoporous alumina surface-modified by a compound in which one or more $C_1$-$C_5$ alkoxy groups are linked to one or more elements selected from the group consisting of Si, Nb, Fe, Co, Zn, Ga and Sn.

In addition, the present invention provides a preparation method of the olefin metathesis catalyst comprising the following steps:

modifying the surface of the mesoporous silica or mesoporous alumina (step 1); and impregnating the surface-modified support of step with rhenium (Re) oxide or molybdenum (Mo) oxide precursor solution, followed by drying and calcining (step 2).

Advantageous Effect

The olefin metathesis catalyst of the present invention allows highly efficient metathesis of long-chain unsaturated hydrocarbons, having at least eight carbons at a low temperature of 150° C. or lower. The catalyst can be separated/recovered readily from reaction solution, regenerated at a low temperature of 400° C. or lower by removing toxins accumulated on it during the metathesis reaction, and used repeatedly in metathesis reaction many times. Therefore the present invention can be made good use in commercial olefin metathesis processes.

DESCRIPTION OF THE PREFERRED EMBODIMENTS

Hereinafter, the present invention is described in detail.

The present invention provides an olefin metathesis catalyst, in which rhenium (Re) oxide or molybdenum (Mo) oxide is supported on a mesoporous silica surface-modified by a compound in which one or more $C_1$-$C_5$ alkoxy groups are linked to one or more metals selected from the group consisting of Al, Nb, Fe, Co, Zn, Ga and Sn.

The present invention also provides an olefin metathesis catalyst, in which rhenium (Re) oxide or molybdenum (Mo) oxide is supported on a mesoporous alumina surface-modified by a compound in which one or more $C_1$-$C_5$ alkoxy groups are linked to one or more elements selected from the group consisting of Si, Nb, Fe, Co, Zn, Ga and Sn.

The olefin metathesis catalyst of the present invention is described in more detail hereinafter.

The olefin metathesis catalyst of the present invention is characterized by using the surface-modified mesoporous silica or mesoporous alumina as a support.

At this time, the surface-modified mesoporous silica or mesoporous alumina support is characterized by comprising an organometallic compound represented by the following formula 1 on the surface thereof.

[Formula 1]

In formula 1 above,

M is at least one element selected from the group consisting of Al, Nb, Fe, Co, Zn, Ga and Sn in the case of the mesoporous silica support, and in the case of the mesoporous alumina support, M is at least one element selected from the group consisting of Si, Nb, Fe, Co, Zn, Ga and Sn;

n is an integer of 2 to 4;

R is $C_1$-$C_5$ alkyl; and

Rs are respectively different or the same.

The mesoporous support can be selected from alumina or silica having a pore size of 30 Å or more. Bio-oils (animal and plant oil, microalgae oil, etc.), which are mainly composed of triglyceride having at least eight carbons, contain unsaturated fatty acid with 1 to 6 double bonds above 50% by volume at least. To metathesis this kind of unsaturated fatty acids having long hydrocarbon chains, the pore size of a catalyst has to be at least 30 Å.

The mesoporous support can be prepared by the conventional method well known to those in the art or a commercially available product can be used. To prepare the support directly, an ionic surfactant such as cetyl bromide or a neutral polymer such as PEO-PPO-PEO block copolymer can be used as a structure directing agent.

The compound used for the surface modification of the support is a compound in which straight or branched $C_2$-$C_5$ alkoxy groups are linked to one or more elements selected from the group consisting of Si, Al, Nb, Fe, Co, Zn, Ga and Sn, but not always limited thereto. The straight or branched $C_2$-$C_5$ alkoxy group indicates normal, iso or tertiary, straight or branched methyl ($CH_3$), ethyl ($C_2H_4$), propyl ($C_3H_6$), butyl ($C_4H_6$), or pentyl ($C_5H_{10}$) alkoxy group.

More particularly, the compound used for the surface modification of the support can be aluminum tributoxide, tetraethyl orthosilicate, niobium isopropoxide, zinc methoxide, iron propoxide, cobalt isopropoxide, gallium isopropoxide or tin isopropoxide.

Herein, the surface modification is defined by the following processes: reacting —OH group on the mesoporous support surface with a metal alkoxy compound (Formula 2), washing out the unreacted metal alkoxy compound, and drying and calcining the support to convert the metal alkoxy compound into metal oxides at the temperature of 500° C. or higher in air atmospheres.

—OH+M-(O—R)$_n$→—O-M-(O—R)$_{n-1}$+ROH     (Formula 2)

M: metal

R: alkyl group

Brønsted acid centers play an important role in generating a metal carbene group (the active site of the reaction) in metathesis catalyst. Meanwhile, Lewis acid centers have been known to increase the activity by changing the electronic structure of the catalyst. In the olefin metathesis catalyst of the present invention, the numbers of these Brønsted and Lewis acid sites increase considerably by means of modifying the support surface and consequently the catalytic activity increases significantly in the course of the olefin metathesis reaction.

Figure 1:
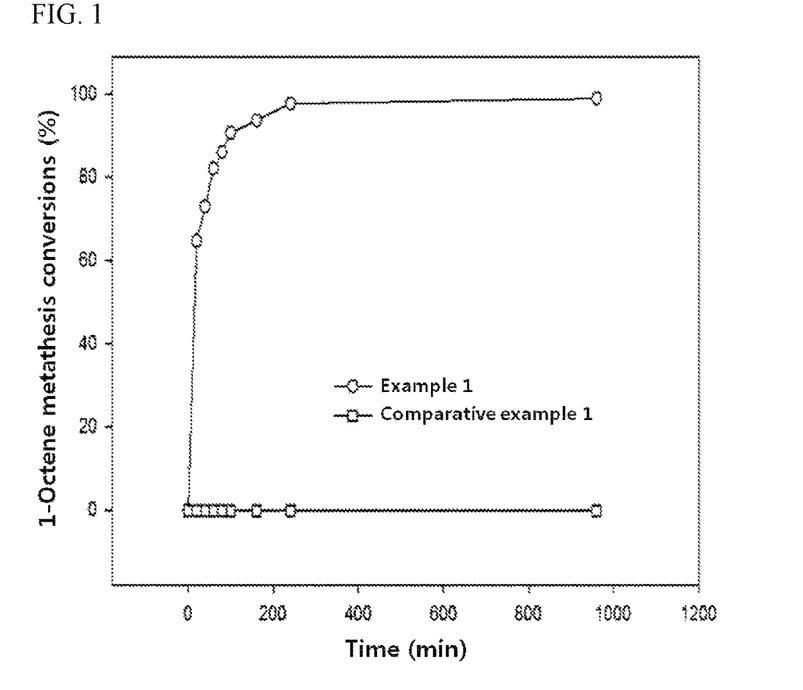
FIG. 1 is a graph illustrating the 1-octene metathesis conversions over the catalysts of example 1 (7 wt % ReO$_3$/Al-SBA 15) and comparative example 1 (7 wt % ReO$_3$/SBA 15) according to time of the reaction.
Figure 2:
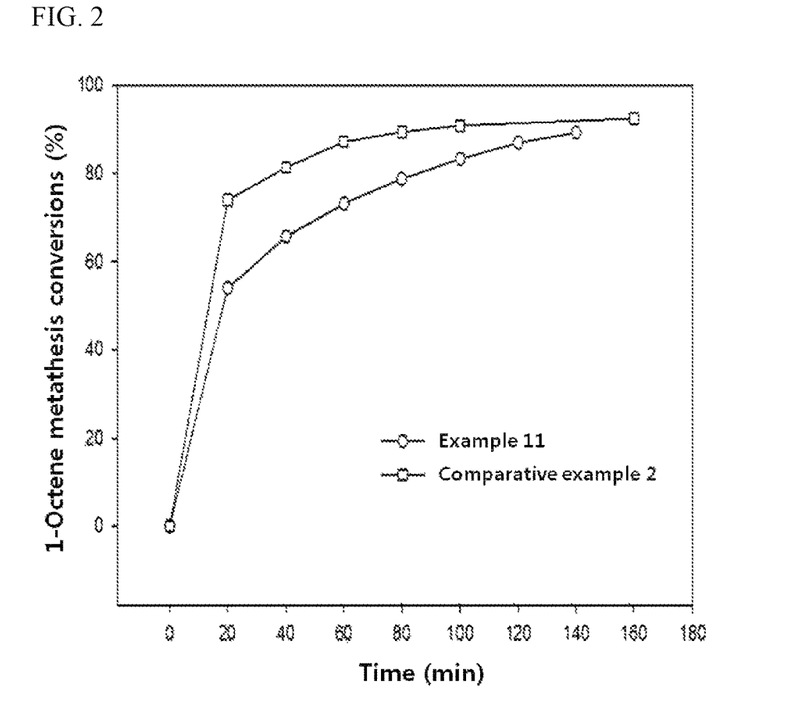
FIG. 2 is a graph illustrating the 1-octene metathesis conversions over the catalysts of example 8 (7 wt % ReO$_x$/Si-mp alumina) and comparative example 2 (7 wt % ReO$_x$/mp alumina) according to time of the reaction.

The olefin metathesis catalyst of the present invention displays a significantly higher initial reaction rate, compared with a catalyst supported on the unmodified support, and a higher final conversion, by virtue of using the surface-modified mesoporous silica or mesoporous alumina support (see experimental example 3, FIG. 1 and FIG. 2).

In the olefin metathesis catalyst of the present invention, rhenium (Re) oxide or molybdenum (Mo) oxide which can facilitate the generation of a metal carbene group, the active site of the reaction, can be used as a catalyst main component.

At this time, the rhenium (Re) oxide or molybdenum (Mo) oxide is preferably loaded at the concentration of 3-20 weight part, more preferably at the concentration of 5-15 weight part by the total weight of the catalyst. When the concentration of the catalyst main component is in the range above, almost all of the cross metathesis reactions can be occurred with a high conversion at a low temperature of 150° C. or lower. If the concentration is less than 3 weight part, the catalytic activity is very low, indicating that the olefin metathesis reaction would not be accomplished efficiently. On the contrary, if the concentration is more than 20 weight part, the crystallite sizes of the Re and Mo oxides become larger, meaning the catalytic activity may also decrease.

In the catalyst according to the present invention, the olefin metathesis catalyst can additionally include one or more platinum group metals selected from the group consisting of platinum (Pt), palladium (Pd) and rhodium (Rh).

The platinum group metal is a component that can be co-loaded for the purpose of efficiently oxidizing and removing the catalyst toxins such as polymers, carbonaceous materials, etc., produced during the olefin metathesis reaction.

The poisoning materials lowering the activity of a catalyst are the impurities such as water present in the reactant and the polymer substance produced by the metathesis polymerization of olefin. When the poisoning materials are accumulated, the catalyst loses its activity gradually owing to the reduction of the main components Re and Mo oxides to metallic forms or the loss of metal carbine group. Thus it is necessary to reoxidize the catalyst at high temperature in order to recover the original metal oxide form for reuse. The poisoning materials of the catalyst are removed by burning in the process above. At this time, if the catalyst contains the platinum group metal on the support, the combustion temperatures of the poisoning materials could be lowered so that the catalyst toxins can be eliminated at a relatively low temperature of 300-400° C.

A preferable concentration of the platinum group metal to be loaded is up to 3 weight part by the total weight of the catalyst and more preferably 0.5-1.5 weight part. If the concentration above is more than 3 weight part, the number of the reaction active sites of the catalyst would be reduced, resulting in the decrease of the catalyst performance.

The olefin metathesis catalyst of the present invention can be reactivated by removing the catalyst toxins at a low temperature of 400° C. or lower without substantially affecting the activity of the metal oxide even if the platinum group metal is additionally loaded (see experimental example 6).

As explained hereinbefore, the olefin metathesis catalyst of the present invention allows highly efficient metathesis of long-chain unsaturated hydrocarbons, having at least eight carbons, at a low temperature of 150° C. or lower. The catalyst can be readily separated/recovered from the reaction solution, oxidized to remove toxins accumulated during the reaction and to recover to the original metal oxides form at a low temperature of 400° C. or lower, and then used again in metathesis reaction for a long time, thereby being made good use in commercial olefin metathesis processes.

In addition, the present invention provides a preparation method of the olefin metathesis catalyst comprising the following steps:
modifying the surface of the mesoporous silica or mesoporous alumina (step 1); and
impregnating the surface-modified support of step 1 with rhenium (Re) oxide or molybdenum (Mo) oxide precursor solution, followed by drying and calcining (step 2).

Hereinafter, the preparation method of the olefin metathesis catalyst of the present invention is described in more detail step by step.

In the preparation method of the olefin metathesis catalyst of the present invention, step 1 is to modify the surface of the mesoporous silica or mesoporous alumina support.

At this time, the surface modification in step 1 comprises the following sub-processes: impregnating the alumina or silica support with $C_1$-$C_5$ alcohol solution containing a compound in which one or more $C_1$-$C_5$ alkoxy groups are linked to one or more elements selected from the group consisting of Al, Si, Nb, Fe, Co, Zn, Ga and Sn (step a); and drying and calcining the support impregnated in step a (step b).

Particularly, the surface modification method according to the present invention is a method for modifying the support by grafting a metal alkoxy compound onto the —OH group present on the support surface, so that the metal alkoxy compound is prevented from being impregnated in other sites of the support surface in order to maximize the numbers of Brønsted and Lewis acid sites.

The surface modification method according to the present invention can regulate the surface modification of the support by adjusting the times of repeat, but it is preferable to perform only one time. If the modification process repeats twice or more, the numbers of Brønsted and/or Lewis acid sites of the support would rather decreased, resulting in the decrease of the catalytic activity.

In the preparation method of the olefin metathesis catalyst of the present invention, step 2 is to impregnate the surface-modified support of step with rhenium (Re) oxide or molybdenum (Mo) oxide precursor solution, followed by drying and calcinations.

At this time, the rhenium (Re) oxide or molybdenum (Mo) oxide precursor is not limited as long as the precursor can be converted into rhenium (Re) oxide or molybdenum (Mo) oxide on the surface-modified alumina or silica support. The rhenium (Re) oxide precursors are preferably exemplified by $HReO_4$, $NH_4ReO_4$, $ReCl_3$ and $CH_3ReO_3$, and the molybdenum (Mo) oxide precursors by $(NH_4)_6Mo_7O_{24}$, $C_6MoO_6$, $MoO_2Cl_2$ and $MoCl_5$.

Drying and calcining the support impregnated with the rhenium oxide or molybdenum oxide precursor can be accomplished by the conventional method, but it is preferable that the catalyst is calcined by supplying air at a temperature of 500° C. or higher after drying at a temperature of 100° C. or lower.

The preparation method of the olefin metathesis catalyst of the present invention is able to modify the surface of a support by grafting a metal alkoxy compound onto the —OH group on the alumina or silica support and can be effectively used as a preparation method that can regulate Brønsted and/or Lewis acid center of the support.

The preparation method of the olefin metathesis catalyst of the present invention can additionally contain a step of impregnating one or more metal precursors selected from the group consisting of platinum (Pt), palladium (Pd) and rhodium (Rh) on the support finished with the step 2 above.

In addition, the present invention provides a method of olefin metathesis reaction to be performed in the presence of the catalyst above.

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Preparative Example 1> Preparation of Mesoporous Silica Support (SBA-15)

24 g of 35% hydrochloric acid aqueous solution and 16 g of P123 block copolymer $(EO)_{20}(PO)_{70}(EO)_{20}$ were added to 500 g of distilled water, which was stirred vigorously to dissolve P123. After completely dissolving P123, 36 ml of tetraethyl orthosilicate was slowly injected with stirring using a syringe pump for 24 hours. The resultant mixture was placed in a Teflon container, and followed by hydrothermal synthesis at 80° C. for 24 hours. The precipitate was washed with anhydrous ethanol twice, dried at 100° C. and calcined at 550° C. for 3 hours in air atmosphere. Finally, the mesoporous silica SBA-15 with an average pore size of 60 Å was obtained.

<Preparative Example 2> Preparation of Mesoporous Alumina Support (Mp-Alumina)

ml of 35% hydrochloric acid aqueous solution and 10 g of P123 were added to 200 ml of anhydrous ethanol, which was stirred vigorously to dissolve P123. After completely dissolving P123, 20.04 g of aluminum isopropoxide was added thereto, and followed by stirring for 5 hours. Next, Anhydrous ethanol was evaporated at 40° C. for 24 hours, and followed by additional evaporation at 80° C. for 24 hours. The mixture was then dried at 100° C. for 2 hours, and calcined at 550° C. for 3 hours in air atmosphere to obtain a mesoporous alumina (mp-alumina) with an average pore size of 80 Å.

<Example 1>~<Example 7> Preparation of Olefin Metathesis Catalyst in which Rhenium Oxide is Supported on the Surface-Modified Mesoporous Silica Step 1: Surface-Modification of Silica Support with Metal Alkoxy Compound 4.7 g of the mesoporous silica support prepared in Preparative Example 1 was added to the mixed solution comprising 10 ml of the metal alkoxy compound shown in Table 1 below and 90 ml of anhydrous isopropanol, and followed by stirring at room temperature for 24 hours. Then, centrifugal separation and washing with anhydrous ethanol of the surface-grafted mesoporous silica were accomplished twice to eliminate the unreacted metal alkoxy compound. The separated wet mesoporous silica was dried at 100° C. for 2 hours, and calcined at 550° C. for 3 hours in air atmosphere to prepare surface-modified SBA-15.

Step 2: Supporting Rhenium Oxide on the Surface-Modified Mesoporous Silica 0.259 g of $NH_4ReO_4$ was dissolved in 22 ml of distilled water, and 3 g of the mesoporous silica surface-modified with the metal alkoxy compound prepared in step 1 was added to this solution to impregnate $NH_4ReO_4$, and followed by drying at 100° C. for hours and calcining at 550° C. for 3 hours in air atmosphere. Following this procedure, the catalyst where $ReO_x$ was loaded 7 weight % was made.

TABLE 1

| | Support | Metal alkoxy compound | Catalyst main component |
|---|---|---|---|
| Example 1 | SBA-15 | Aluminum-tri-sec-butoxide | Re |
| Example 2 | SBA-15 | Niobium isopropoxide | Re |
| Example 3 | SBA-15 | Zinc methoxide | Re |
| Example 4 | SBA-15 | Iron propoxide | Re |
| Example 5 | SBA-15 | Cobalt isopropoxide | Re |
| Example 6 | SBA-15 | Gallium isopropoxide | Re |
| Example 7 | SBA-15 | Tin isopropoxide | Re |

<Example 8>~<Example 14> Preparation of Olefin Metathesis Catalyst in which Rhenium Oxide is Supported on the Surface-Modified Mesoporous Alumina Step 1: Surface-Modification of Mesoporous Alumina with Metal Alkoxy Compound 5 g of the mesoporous alumina (mp alumina) prepared in Preparative Example 2 was added to the mixed solution comprising 10 ml of the metal alkoxy compound shown in Table 2 below and 90 ml of anhydrous isopropanol, and followed by stirring at room temperature for 24 hours. Then, centrifugal separation and washing with anhydrous ethanol of the surface-grafted mesoporous were carried out twice to eliminate the unreacted metal alkoxy compound. After this, the wet mesoporous alumina was dried at 100° C. for 2 hours, and calcined at 550° C. for 3 hours in air atmosphere to obtain surface-modified mesoporous alumina.

Step 2: Supporting Rhenium Oxide on the Surface-Modified Mesoporous Alumina 0.259 g of $NH_4ReO_4$ was dissolved in 22 ml of distilled water, and 3 g of the mesoporous alumina surface-modified with the metal alkoxy compound prepared in step 2 was added to this solution to impregnate $NH_4ReO_4$, and followed by drying at 100° C. for hours and calcining at 550° C. for 3 hours in air atmosphere. From this the catalyst in which $ReO_x$ was loaded 7 weight % was made.

TABLE 2

| | Support | Metal alkoxy compound | Catalyst main component |
|---|---|---|---|
| Example 8 | mp alumina | Tetraethyl orthosilicate | Re |
| Example 9 | mp alumina | Niobium isopropoxide | Re |
| Example 10 | mp alumina | Zinc methoxide | Re |
| Example 11 | mp alumina | Iron propoxide | Re |
| Example 12 | mp alumina | Cobalt isopropoxide | Re |
| Example 13 | mp alumina | Gallium isopropoxide | Re |
| Example 14 | mp alumina | Tin isopropoxide | Re |

<Example 15> Preparation of Olefin Metathesis Catalyst in which Molybdenum Oxide is Supported on the Surface-Modified Mesoporous Silica 0.185 g of ammonium heptamolybdate was dissolved in 20 ml of distilled water, and 2 g of the mesoporous silica (Al-SBA 15) surface-modified with aluminum-tri-sec-butoxide prepared in step 1 of Example 1 was added to this solution to impregnate ammonium heptamolybdate, and followed by drying at 100° C. for 2 hours and calcining at 550° C. for 2 hours in air atmosphere. From this the catalyst where molybdenum oxide was loaded 7 weight % was prepared (7 wt % $MoO_x$/Al-SBA 15).

<Example 16> Preparation of Olefin Metathesis Catalyst in which Molybdenum Oxide, Platinum (Pt), Palladium (Pd) and Rhodium (Rh) are Supported on the Surface-Modified Mesoporous Silica 0.076 g of platinum acetylacetonate, 0.057 g of palladium acetylacetonate and 0.078 g of rhodium acetylacetonate were dissolved in 36 ml of toluene, and 5 g of the catalyst (7 wt % $ReO_x$/Al-SBA 15) prepared in Example 1 was added to this solution, and followed by drying at 100° C. for 2 hours and calcining at 550° C. for 3 hours in air atmosphere. As a result of this, the catalyst in which platinum group metals (Pt, Pd and Rh) were loaded 1.2 weight % was obtained (7 wt % $ReO_x$/1.2 wt % Pt, Pd, Rh/Al-SBA 15).

<Comparative Example 1> Preparation of Olefin Metathesis Catalyst Containing Mesoporous Silica and Rhenium Oxide 0.259 g of $NH_4ReO_4$ was dissolved in 22 ml of distilled water, and 3 g of the mesoporous silica (SBA-15) prepared in Preparative Example 1 was added to this solution, and followed by drying at 100° C. for hours and calcining at 550° C. for 3 hours in air atmosphere. As a result, the catalyst in which $ReO_x$ was loaded 7 weight % was prepared (7 wt % $ReO_x$/SBA 15).

<Comparative Example 2> Preparation of Olefin Metathesis Catalyst Containing Mesoporous Alumina and Rhenium Oxide 0.259 g of $NH_4ReO_4$ was dissolved in 22 ml of distilled water, and 3 g of the alumina support (mp alumina) prepared in Preparative Example 2 was added to this solution, and followed by drying at 100° C. for hours and calcining at 550° C. for 3 hours in air atmosphere to prepare the catalyst where $ReO_x$ was loaded 7 weight % (7 wt % $ReO_x$/mp alumina).

<Experimental Example 1> Support Changing Experiment

To evaluate the catalytic activity of the olefin metathesis catalyst of the present invention according to the changes of the support, the following experiment was conducted.

Particularly, 1 g of the catalyst supported on mesoporous silica (7 wt % $ReO_x$/Al-SBA 15) surface-modified with the Al alkoxy compound prepared in Example 1 was placed in a reactor. Then, air was fed to the reactor at the flow rate of 150 ml/min. The temperature of the reactor was raised to 550° C. at a ramp rate of 5° C./min and then maintained at 550° C. for 2 hours. Then, the air was replaced with nitrogen at 550° C., and followed by heating for 2 hours at the flow rate of 150 ml/min in order to partially reducing the rhenium oxide. After this the temperature was lowered to room temperature. Next, 50 µl of the reaction promoter tetrabutyltin was added to the reactor to activate the catalyst for 20 minutes, together with 2 g of heptane as solvent and a GC analysis standard material. 8 g of the reactant 1-octene was added thereto, and then 1-octene self-metathesis was conducted with stirring at 25° C. in nitrogen atmosphere. To calculate the conversion of 1-octene into 7-tetradecene, samples were regularly taken and quantitatively analyzed by GC (HP innowax 30 column). The results are shown in Table 3 below.

The conversion was calculated by Formula 3 below.

$$100(X0-X)/X0 \qquad \text{(Formula 3)}$$

X0: initial amount of 1-octene

X: amount of 1-octene remaining until analysis

1-Octene self-metathesis was carried out by the same manner as described above using the catalyst (7 wt % $ReO_x$/Si-mp alumina) supported on the mesoporous alumina surface-modified with tetraethyl orthosilicate prepared in Example 8. The results are shown in Table 4.

TABLE 3

| Time (min) | 20 | 40 | 60 | 80 | 100 | 160 | 240 | 840 |
|---|---|---|---|---|---|---|---|---|
| Conversion (%) | 64.9 | 76.9 | 82.1 | 86.0 | 90.7 | 93.6 | 97.7 | 99.0 |

TABLE 4

| Time (min) | 20 | 40 | 60 | 80 | 100 | 160 | 360 | 720 |
|---|---|---|---|---|---|---|---|---|
| Conversion (%) | 74.0 | 81.4 | 87.2 | 89.5 | 90.9 | 92.5 | 92.6 | 92.8 |

As shown in Table 3, the catalyst in which rhenium oxide was supported on the surface-modified mesoporous silica according to the present invention demonstrated a fast initial reaction conversion 20 minutes after the start of the reaction. After 4 hours from the start of the reaction, the conversion was about 99%, indicating that the activity was maintained for a long time.

As shown in Table 4, the catalyst in which rhenium oxide was supported on the surface-modified mesoporous alumina according to the present invention demonstrated a fast initial reaction conversion 20 minutes after the start of the reaction and the catalytic activity was maintained for a long time.

Therefore, the surface-modified mesoporous silica or mesoporous alumina was confirmed to be appropriate as a support for the catalyst of the present invention.

<Experimental Example 2> Experiment of Catalyst Main Component Change g of the molybdenum oxide catalyst prepared in Example 15 (7 wt % $MoO_x$/Al-SBA 15) was loaded in a reactor, which was partially reduced by the same manner as described in Experimental Example 1. Then, 50 µl of the reaction promoter tetrabutyltin were added to the reactor together with 2 g of toluene to activate the catalyst for 20 minutes. 8 g of the reactant 1-octene was added thereto, and then the metathesis reaction was done with stirring at 100° C. in nitrogen atmosphere.

According to the GC analysis, the conversion of 1-octene into 7-tetradecene over the molybdenum oxide catalyst was 62.6% after 20 minutes of the reaction.

Therefore, it was confirmed that the molybdenum oxide as a main component of the catalyst of the present invention had excellent activity.

<Experimental Example 3> Experiment of Metathesis Reaction Change

Self-metathesis reaction was conducted by the same manner as described in Experimental Example 1 except that the reaction temperature was 50° C. and 1-decene and methyl oleate were used as reactants instead of 1-octene. The conversion over the catalyst of Example 1 (7 wt % $ReO_x$/Al-SBA 15) was measured after minutes from the reaction started by the same manner as described in Experimental Example 1.

As a result, the conversion of 1-decene into 9-octadecene was 81.6% after 20 minutes from the start of 1-decene metathesis, while the conversion of methyl oleate into 9-octadecene and 9-octadecene-1,18-dioate was 21.2% for the initial 20 minutes of the reaction.

Therefore, it was confirmed that the olefin metathesis catalyst of the present invention had excellent activity for various reactants.

<Experimental Example 4> Effect of Support Surface Modification

To evaluate the effect of support surface modification on the catalytic activity, 1-octene metathesis reaction was carried out by the same manner as described in Experimental Example 1 in the presence of the catalysts of Example 1 (7 wt % ReO$_x$/Al-SBA 15), Comparative Example 1 (7 wt % ReO$_x$/SBA 15), Example 8 (7 wt % ReO$_x$/Si-mp alumina) and Comparative Example 2 (7 wt % ReO$_x$/mp alumina) respectively. The results are shown in FIG. 1 and FIG. 2.

FIG. 1 is a graph illustrating the 1-octene metathesis conversion over the catalysts of example 1 (7 wt % ReO$_3$/Al-SBA 15) and comparative example 1 (7 wt % ReO$_3$/SBA 15) with the reaction time.

FIG. 2 is a graph illustrating the 1-octene metathesis conversion of the catalysts of example 8 (7 wt % ReO$_x$/Si-mp alumina) and comparative example 2 (7 wt % ReO$_x$/mp alumina) with the reaction time.

As shown in FIG. 1, the conversion over the catalyst in which Re oxide was supported on a surface-unmodified mesoporous silica (Comparative Example 1) was nearly 0% until 16 hours from the reaction started. On the contrary, the conversion over the catalyst in which Re oxide was supported on a surface-modified mesoporous silica of the present invention (Example 1) was approaching 99% 4 hours after the reaction started and the catalytic activity was maintained for a long time.

As shown in FIG. 2, the conversion over the catalyst in which Re oxide was supported on a surface-unmodified mesoporous alumina (Comparative Example 2) was 54% 20 minutes after the reaction started. Whereas the conversion over the catalyst in which Re oxide was supported on a surface-modified mesoporous alumina of the present invention (Example 8) was 74% 20 minutes after the reaction started.

Therefore, it was confirmed that the catalyst in which rhenium (Re) oxide was supported on a surface-modified support of the present invention showed significantly faster reaction speed and was able to maintain a high conversion during a long reaction time, suggesting that the surface-modification was effective.

<Experimental Example 5> Effect of Various Metal Alkoxy Compounds on Surface Modification To evaluate the effect of various metal alkoxy compounds on surface modification, 1-octene metathesis reaction was carried out in the presence of the catalysts prepared in Examples 2-14 by the same manner as described in Experimental Example 1. The conversion was investigated 20 minutes after the reaction started. The results are shown in Table 5. As shown in Table 5, the catalyst in which Re oxide was supported on SBA-15 or mesoporous alumina surface-modified with Nb, Zn, Fe, Co, Ga or Sn alkoxy compound showed higher conversion 20 minutes after the reaction started than the catalysts of Comparative Example 1 (7 wt % ReO$_x$/SBA 15) and Comparative Example 2 (7 wt % ReO$_x$/mp alumina) whose surfaces were not modified. Therefore, it was confirmed that the surface modification of SBA-15 and mesoporous alumina support with the metal alkoxy compound of the present invention was effective.

TABLE 5

| Example | Surface-modified support | 20 min. conversion (%) |
| --- | --- | --- |
| Example 2 | Nb-SBA-15 | 20.3 |
| Example 3 | Zn-SBA-15 | 48.8 |
| Example 4 | Fe-SBA-15 | 47.9 |
| Example 5 | Co-SBA-15 | 46.4 |
| Example 6 | Ga-SBA-15 | 60.5 |
| Example 7 | Sn-SBA-15 | 35.3 |
| Example 9 | Nb-mp alumina | 75.5 |
| Example 10 | Zn-mp alumina | 55.7 |
| Example 11 | Fe-mp alumina | 59.6 |
| Example 12 | Co-mp alumina | 61.4 |
| Example 13 | Ga-mp alumina | 72.1 |
| Example 14 | Sn-mp alumina | 59.8 |

<Experimental Example 6> Effect of Platinum Group Metal

The following experiment was conducted to evaluate the catalytic activity of the catalyst of the present invention prepared by co-loading a platinum group metal as a component selected from the group consisting of platinum (Pt), palladium (Pd) and rhodium (Rh) in order to oxidize catalyst toxins accumulated during the metathesis reaction.

Particularly, 1 g of the prepared catalyst of Example 16 (7 wt % ReO$_x$/1.2 wt % Pt, Pd, Rh/Al-SBA 15) was placed in a reactor. Then 1-octene metathesis reaction was carried out by the same manner as described in Experimental Example 1. After this first reaction the catalyst was separated from the reaction solution by using a centrifuge and the 1-octene metathesis reaction was newly begun after loading the separated catalyst and new reactant into a clean reactor. This reaction and catalyst separation cycle was repeated 5 times to investigate the catalyst deactivation with time.

The conversions of each metathesis reactions, performed 5 times in total, were respectively 98%, 97%, 91%, 82% and 67%, 5 hours after the reaction started, indicating that the catalyst was gradually degraded as reaction repeated.

After the 5$^{th}$ reaction, the deactivated catalyst was separated from the reaction solution, and heat-treated at 380° C. for 2 hours to oxidize toxins in the air atmosphere flowing at a rate of 200 ml/min, and followed by reduction for 2 hours in nitrogen (200 ml/min) atmosphere. Then, 6$^{th}$ 1-octene metathesis reaction was performed by the same manner as described in Experimental Example 1. The conversion was measured after 5 hours from the reaction started.

As the result of GC analysis, the conversion was 97.8% similar to that of the first reaction.

Therefore, it was confirmed that the platinum group metal loaded 1.2 weight % did not affect the activity of the rhenium oxide being the main component of the catalyst. To eliminate catalyst toxins, a high temperature of 500° C. or higher is required in general. However, the co-loading of the platinum group metal was able to remove catalyst toxins at a low temperature of up to 400° C. and could be reactivated thereafter.

<Experimental Example 7> Effect of Number of Surface Modification

To investigate the effect of the number of surface modification done on a support on the catalytic activity, the surface of the mesoporous silica support prepared in Preparative Example 1 (SBA-15) was grafted with aluminum-tri-sec-butoxide and calcined by the same manner as described in step 1 of Example 1. The grafting and calcining were repeated one to three times. 7 weight % of rhenium oxide catalysts supported on these surface-modified mesoporous silicas was prepared by the same manner as described in step 2 of Example 1. Then, the conversions of 1-octene were measured 20 minutes after the reaction started by the same manner as described in Experimental Example 1.

According to GC analyses, the conversions over the catalysts where the silica support surface was modified once, twice and three times were 64.9%, 59.5% and 48.3% respectively.

Therefore, it was confirmed that as the surface modification repeated, the catalytic activity of a catalyst decreased, indicating that only when the metal alkoxy compound was selectively grafted to —OH group on the surface of a support, the surface modification effect was most pronounced in the metathesis reaction.

What is claimed is:

1. A method of olefin metathesis comprising the step of contacting olefin with an olefin metathesis catalyst, in which rhenium (Re) oxide or molybdenum (Mo) oxide is supported on the surface-modified mesoporous silica support which is surface modified with an oxide of an element selected from the group consisting of Al, Nb, Fe, Co, Zn, Ga and Sn, and characteristically prepared by the processes of:
    reacting the —OH group existing on the surface of the mesoporous silica support with a compound in which 1~4 $C_1$-$C_5$ alkoxy groups are linked to the element selected from the group consisting of Al, Nb, Fe, Co, Zn, Ga and Sn in order to graft the compound on the surface of the support; and eliminating the unreacted compounds from the support, followed by calcining; and
    impregnating the mesoporous silica support with a rhenium (Re) oxide or molybdenum (Mo) oxide precursor solution, followed by calcining, to convert the rhenium (Re) oxide or molybdenum (Mo) oxide precursor to rhenium (Re) oxide or molybdenum (Mo) oxide on the surface modified silica support;
the catalyst additionally containing one or more platinum group metals selected from the group consisting of Pt, Pd and Rh, at a concentration of 3 weight part or less, by total weight of the catalyst.

2. The method of olefin metathesis according to claim 1, wherein the catalyst provides at least about 90.7% conversion during olefin metathesis.

3. A method of olefin metathesis comprising the step of contacting olefin with an olefin metathesis catalyst, in which rhenium (Re) oxide or molybdenum (Mo) oxide is supported on the surface-modified mesoporous alumina support which is surface modified with an oxide of an element selected from the group consisting of Si, Nb, Fe, Co, Zn, Ga and Sn, and characteristically prepared by the processes of:
    reacting the —OH group existing on the surface of the mesoporous alumina support with a compound in which 1~4 $C_1$-$C_5$ alkoxy groups are linked to the element selected from the group consisting of Si, Nb, Fe, Co, Zn, Ga and Sn in order to graft the compound on the surface of the support; and eliminating the unreacted compounds from the support, followed by calcining; and
    impregnating the mesoporous silica support with a rhenium (Re) oxide or molybdenum (Mo) oxide precursor solution, followed by calcining, to convert the rhenium (Re) oxide or molybdenum (Mo) oxide precursor to rhenium (Re) oxide or molybdenum (Mo) oxide on the surface modified alumina support;
the catalyst additionally containing one or more platinum group metals selected from the group consisting of Pt, Pd and Rh, at a concentration of 3 weight part or less, by total weight of the catalyst.

4. The method of olefin metathesis according to claim 3, wherein the catalyst provides at least about 90.9% conversion during olefin metathesis.

5. A method of olefin metathesis of unsaturated hydrocarbons having at least 8 carbons, at relatively low temperature, the method comprising:
    providing an olefin metathesis catalyst comprising:
        a surface-modified mesoporous support that comprises silica or alumina;
            wherein when the support is a silica support, the support is surface-modified with an oxide of one or more metal elements selected from the group consisting of Al, Nb, Fe, Co, Zn, Ga, and Sn;
            wherein when the support is an alumina support, the support is surface-modified with an oxide of one or more metal elements selected from the group consisting of Si, Nb, Fe, Co, Zn, Ga, and Sn;
        the surface-modified mesoporous support being prepared by:
            reacting an —OH group on a surface of the mesoporous support with a compound in which 1~4 $C_1$-$C_5$ alkoxy groups are linked to the metal element in order to graft a metal alkoxy compound onto the surface of the mesoporous support;
            eliminating unreacted compound from the support, followed by calcining to convert the metal alkoxy compound to a metal oxide;
            impregnating the surface-modified support with at least one of a rhenium (Re) oxide or molybdenum (Mo) oxide precursor solution, followed by calcining to convert the rhenium (Re) oxide or molybdenum (Mo) oxide precursor to rhenium (Re) oxide or molybdenum (Mo) oxide;
            impregnating the surface-modified support with one or more platinum group metals selected from the group consisting of Pt, Pd, and Rh;
        wherein the olefin metathesis catalyst includes at least one of rhenium (Re) oxide or molybdenum (Mo) oxide in an amount of 3% to 20% by weight;
        wherein the olefin metathesis catalyst includes the one or more platinum group metals in an amount of 0.5% to 3% by weight; and
        wherein the olefin metathesis catalyst has an average pore size of 30 Å to about 80 Å;
    contacting an olefin with the catalyst at a temperature of 150° C. or less to produce an olefin having at least 8 carbons;
        wherein the catalyst provides at least about 90.7% conversion during olefin metathesis, within a reaction time of no more than about 100 minutes.

6. The method of claim 5, the method further comprising removing toxins accumulated on the catalyst during the metathesis reaction, by regenerating the catalyst by exposure to a temperature of 400° C. or less for a period of 2 hours.

7. A preparation method for an olefin metathesis catalyst in which rhenium (Re) oxide or molybdenum (Mo) oxide is supported on the surface-modified mesoporous silica support which is surface modified with an oxide of an element selected from the group consisting of Al, Nb, Fe, Co, Zn, Ga and Sn, and characteristically prepared by the processes of: reacting the —OH group existing on the surface of the mesoporous silica support with a compound in which 1~4 $C_1$-$C_5$ alkoxy groups are linked to the element selected from the group consisting of Al, Nb, Fe, Co, Zn, Ga and Sn in order to graft the compound on the surface of the support; and eliminating the unreacted compounds from the support, followed by calcining; and impregnating the mesoporous silica support with a rhenium (Re) oxide or molybdenum (Mo) oxide precursor solution, followed by calcining, to convert the rhenium (Re) oxide or molybdenum (Mo) oxide precursor to rhenium (Re) oxide or molybdenum (Mo) oxide on the surface modified silica support; the catalyst additionally containing one or more platinum group metals selected from the group consisting of Pt, Pd and Rh, at a concentration of 3 weight part or less, by total weight of the catalyst, the preparation method comprising the following steps:

modifying the surface of the mesoporous silica comprising reacting an —OH group present on the surface with a compound in which one or more $C_1$-$C_5$ alkoxy groups are linked to one or more elements selected from the group consisting of Al, Nb, Fe, Co, Zn, Ga and Sn, removing the unreacted compound from the support and then calcining to bond the one or more elements to the surface of the mesoporous silica support (step 1);

impregnating the surface-modified support of step 1 with rhenium (Re) oxide or molybdenum (Mo)oxide precursor solution, followed by drying and calcining (step 2); and impregnating the support with a precursor solution comprising one or more metals selected from the group consisting of Pt, Pd, and Rh (step 3).

8. The method according to claim 7, wherein the $C_1$-$C_5$ alkoxy groups linked to one or more elements selected from the group consisting of Al, Nb, Fe, Co, Zn, Ga and Sn are represented by formula 1 below:

[Formula 1]

In formula 1 above,
M is at least one element selected from the group consisting of Al, Nb, Fe, Co, Zn, Ga and Sn;
n is an integer of 2 to 4;
R is $C_1$-$C_5$ alkyl, and when n is 3 or 4, they may be respectively different or the same.

9. A preparation method for an olefin metathesis catalyst in which rhenium (Re) oxide or molybdenum (Mo) oxide is supported on the surface-modified mesoporous alumina support which is surface modified with an oxide of an element selected from the group consisting of Si, Nb, Fe, Co, Zn, Ga and Sn, and characteristically prepared by the processes of: reacting the —OH group existing on the surface of the mesoporous alumina support with a compound in which 1~4 $C_1$-$C_5$ alkoxy groups are linked to the element selected from the group consisting of Si, Nb, Fe, Co, Zn, Ga and Sn in order to graft the compound on the surface of the support; and eliminating the unreacted compounds from the support, followed by calcining; and impregnating the mesoporous silica support with a rhenium (Re) oxide or molybdenum (Mo) oxide precursor solution, followed by calcining, to convert the rhenium (Re) oxide or molybdenum (Mo) oxide precursor to rhenium (Re) oxide or molybdenum (Mo) oxide on the surface modified alumina support; the catalyst additionally containing one or more platinum group metals selected from the group consisting of Pt, Pd and Rh, at a concentration of 3 weight part or less, by total weight of the catalyst, the preparation method comprising the following steps:

modifying the surface of the mesoporous alumina comprising reacting an —OH group present on the surface with a compound in which one or more $C_1$-$C_5$ alkoxy groups are linked to one or more elements selected from the group consisting of Si, Nb, Fe, Co, Zn, Ga and Sn, removing the unreacted compound from the support and then calcining to bond the one or more elements to the surface of the mesoporous alumina support (step 1);

impregnating the surface-modified support of step 1 with rhenium (Re) oxide or molybdenum (Mo) oxide precursor solution, followed by drying and calcining (step 2); and impregnating the support with a precursor solution comprising one or more metals selected from the group consisting of Pt, Pd, and Rh (step 3).

10. The method according to claim 9, wherein the $C_1$-$C_5$ alkoxy groups linked to one or more elements selected from the group consisting of Si, Nb, Fe, Co, Zn, Ga and Sn are represented by formula 1 below:

[Formula 1]

In formula 1 above,
M is at least one element selected from the group consisting of Si, Nb, Fe, Co, Zn, Ga and Sn;
n is an integer of 2 to 4;
R is $C_1$-$C_5$ alkyl, and when n is 3 or 4, they may be respectively different or the same.

* * * * *